(12) United States Patent
Wang et al.

(10) Patent No.: US 12,279,805 B2
(45) Date of Patent: *Apr. 22, 2025

(54) METHOD FOR DETECTING PRESENCE OF TUBING IN PUMP ASSEMBLY

(71) Applicant: Avent, Inc., Alpharetta, GA (US)

(72) Inventors: Ruoya Wang, Decatur, GA (US); Ken Driver, Brookhaven, GA (US)

(73) Assignee: Avent, Inc., Alpharetta, GA (US)

( * ) Notice: Subject to any disclaimer, the term of this patent is extended or adjusted under 35 U.S.C. 154(b) by 219 days.

This patent is subject to a terminal disclaimer.

(21) Appl. No.: 18/103,172

(22) Filed: Jan. 30, 2023

(65) Prior Publication Data

US 2023/0248413 A1 Aug. 10, 2023

Related U.S. Application Data

(63) Continuation of application No. 16/233,246, filed on Dec. 27, 2018, now Pat. No. 11,564,731.

(51) Int. Cl.
*A61B 18/14* (2006.01)
*F04B 43/12* (2006.01)
(Continued)

(52) U.S. Cl.
CPC ............. *A61B 18/14* (2013.01); *F04B 43/12* (2013.01); *F04B 51/00* (2013.01); *G16H 40/63* (2018.01);
(Continued)

(58) Field of Classification Search
CPC ................ A61B 18/1206; A61B 18/14; A61B 2018/00023; A61B 2018/00029;
(Continued)

(56) References Cited

U.S. PATENT DOCUMENTS

2004/0230384 A1 11/2004 Haynes
2013/0267894 A1 10/2013 Woolford
(Continued)

FOREIGN PATENT DOCUMENTS

EP 2942023 A2 11/2015
JP 2010159974 A 7/2010

OTHER PUBLICATIONS

International Search Report and Written Opinion for PCT/US2019/067426, dated Apr. 17, 2020, 22 pages.

*Primary Examiner* — George Manuel
(74) *Attorney, Agent, or Firm* — Meunier Carlin & Curfman LLC

(57) ABSTRACT

Methods for detecting tubing in a pump assembly of a pump system are provided. For example, a method comprises connecting a power supply to each of a plurality of pump motors of the pump system. Each pump motor of the plurality of pump motors has a power supply cable configured to connect to the power supply and drives a pump head of a plurality of pump heads of the pump system. The method also comprises sensing a motor current from each of the power supply cables, determining whether tubing is loaded in each pump head, and, if tubing is not loaded in a pump head, then disconnecting from the power supply the power supply cable of the pump motor associated with the pump head in which tubing is not loaded. Systems for detecting the presence of tubing within a pump head of a plurality of pump heads also are provided.

20 Claims, 7 Drawing Sheets

(51) Int. Cl.
*F04B 51/00* (2006.01)
*G16H 40/63* (2018.01)
*A61B 18/00* (2006.01)

(52) U.S. Cl.
CPC ............... *A61B 2018/00023* (2013.01); *A61B 2018/00642* (2013.01); *A61B 2018/00708* (2013.01); *A61B 2018/00827* (2013.01)

(58) Field of Classification Search
CPC ........... A61B 2018/00035; A61B 2018/00642; A61B 2018/00708; A61B 2018/00791; A61B 2018/00827; A61N 1/36021; F04B 43/12; F04B 49/06; F04B 51/00; F04B 53/22; G05B 15/02; G16H 40/63
See application file for complete search history.

(56) References Cited

U.S. PATENT DOCUMENTS

2015/0320481 A1 11/2015 Cosman, Jr.
2018/0119692 A1* 5/2018 Bangor ................. E21B 47/107

* cited by examiner

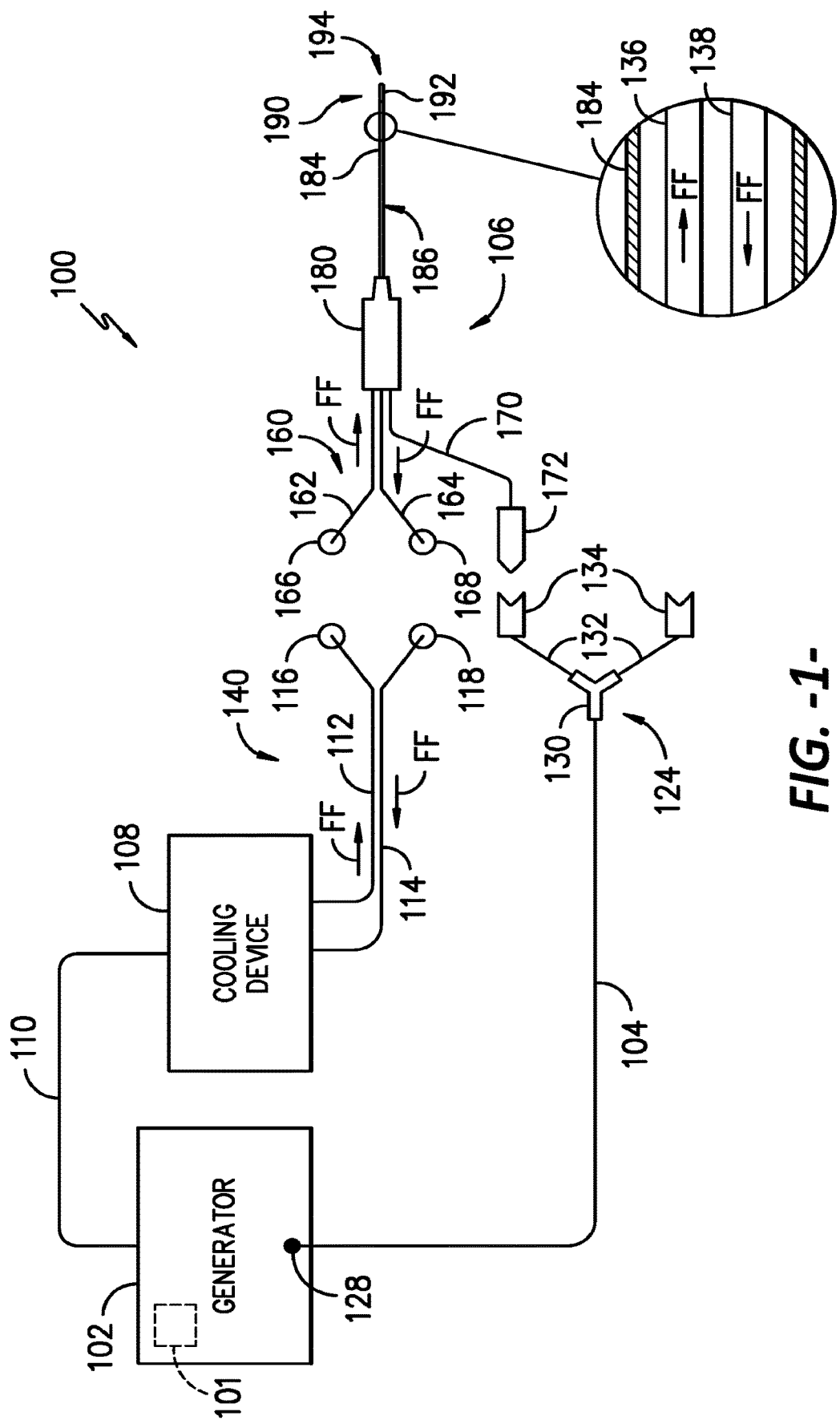
FIG. -1-

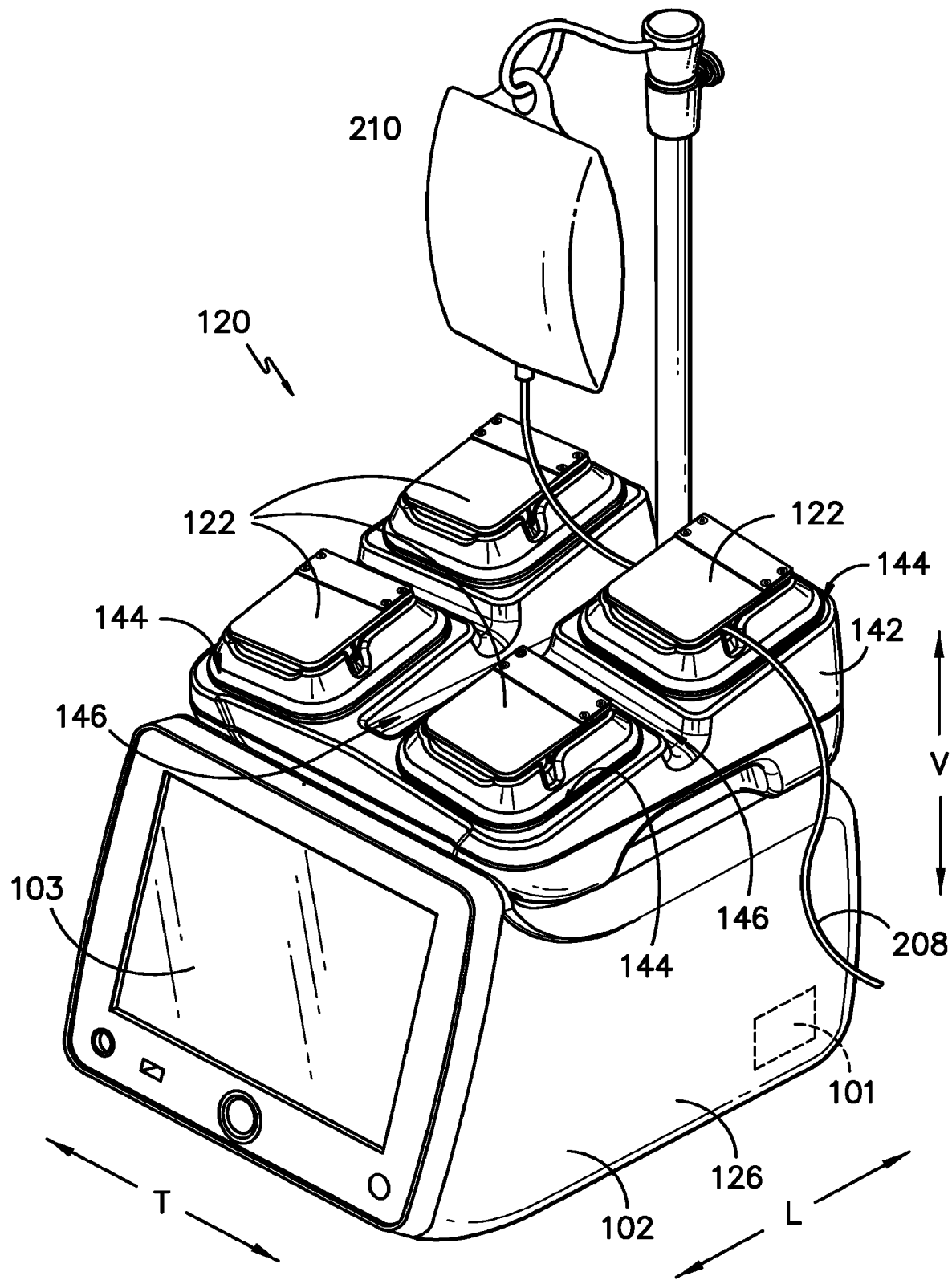
FIG. -2-

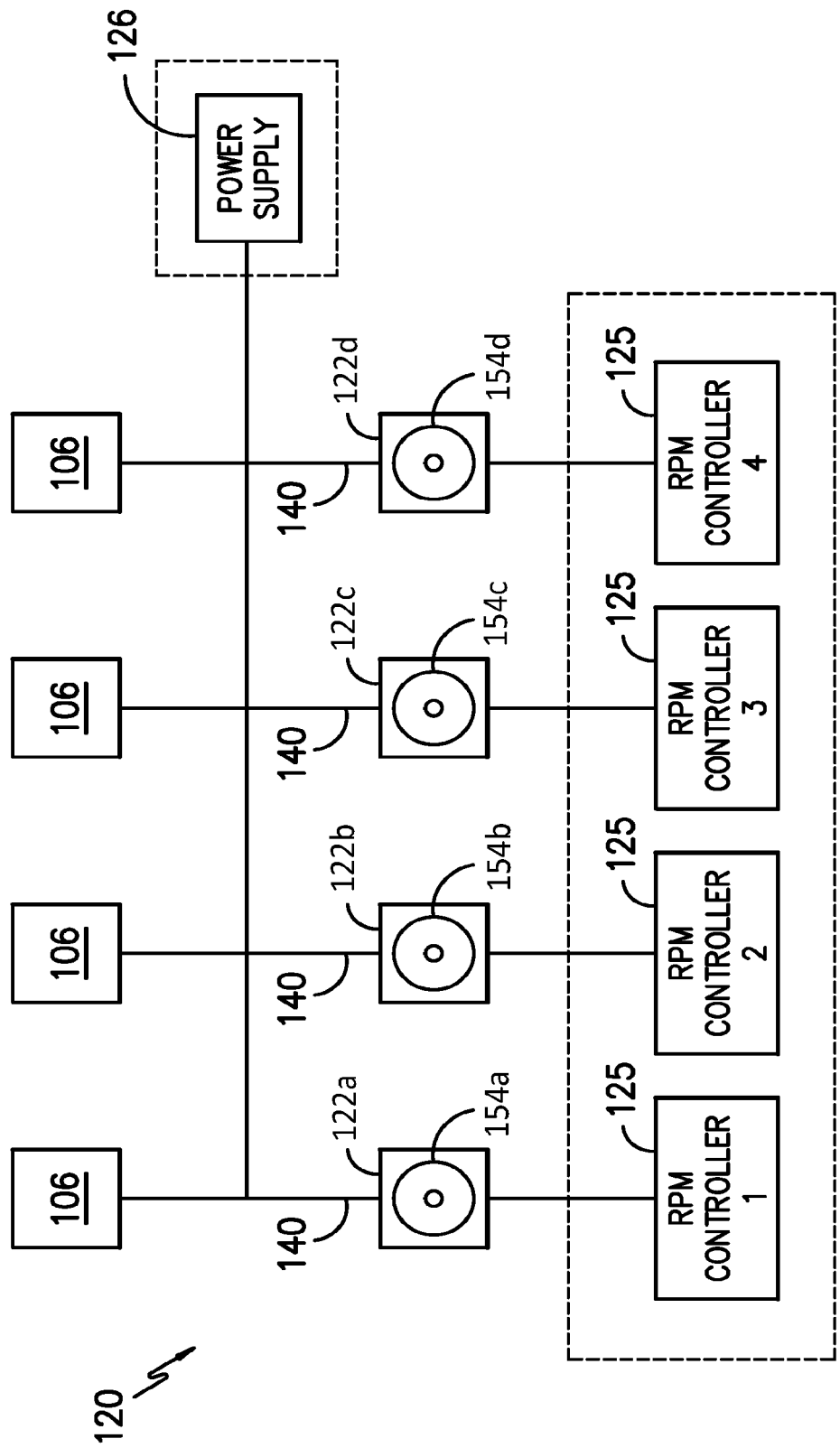
FIG. -3-

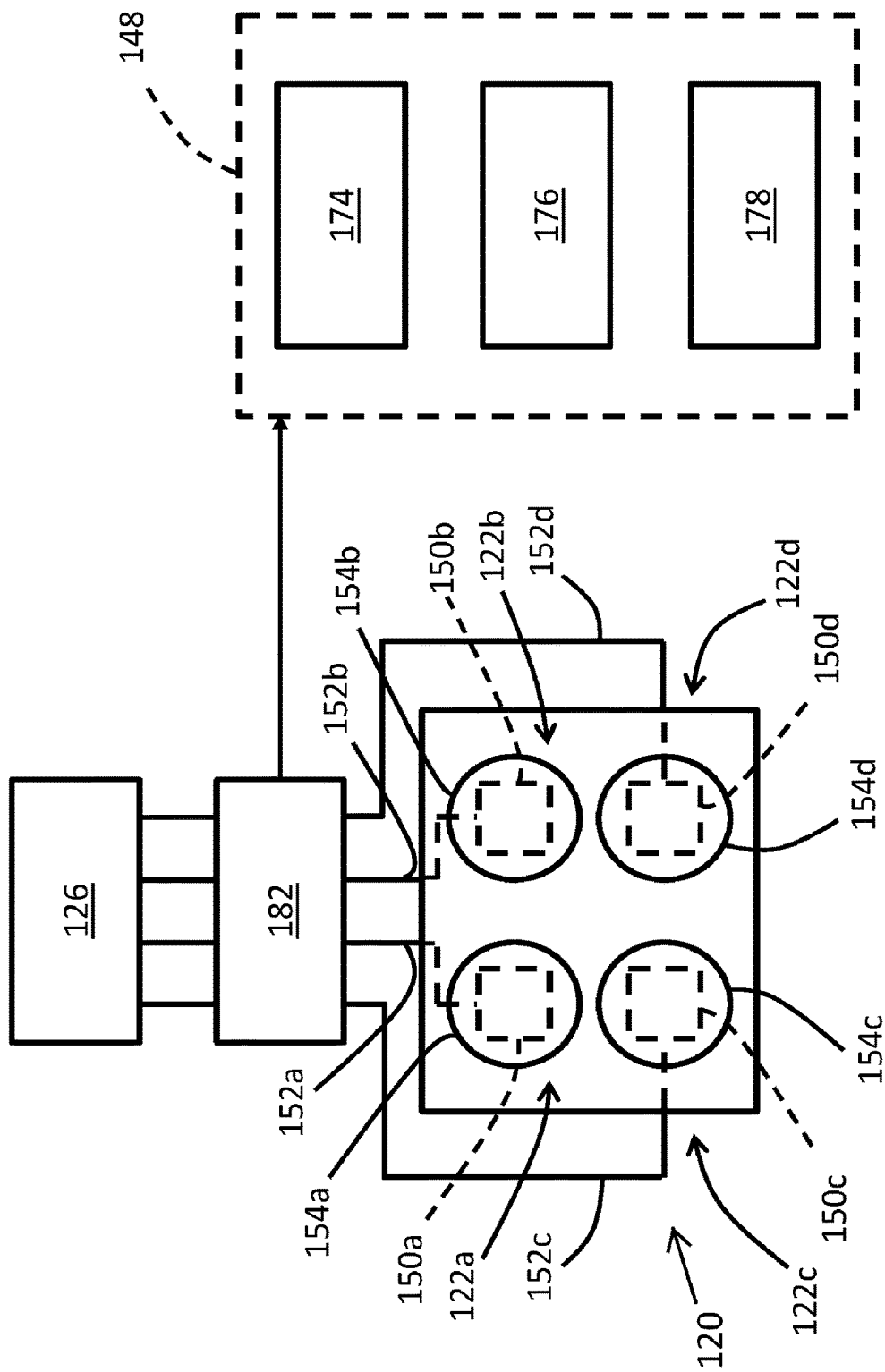
FIG. -4-

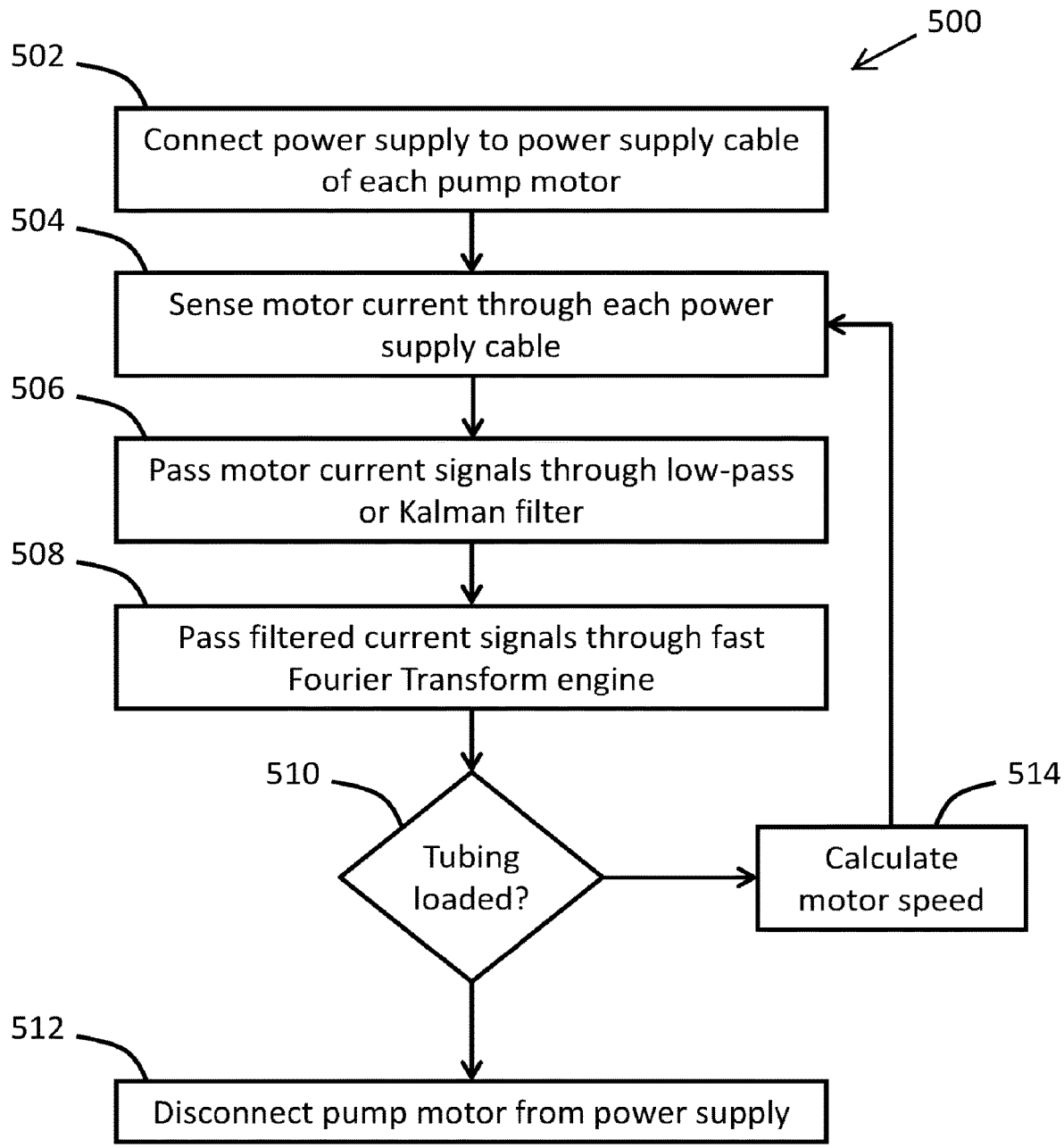
FIG. -5-

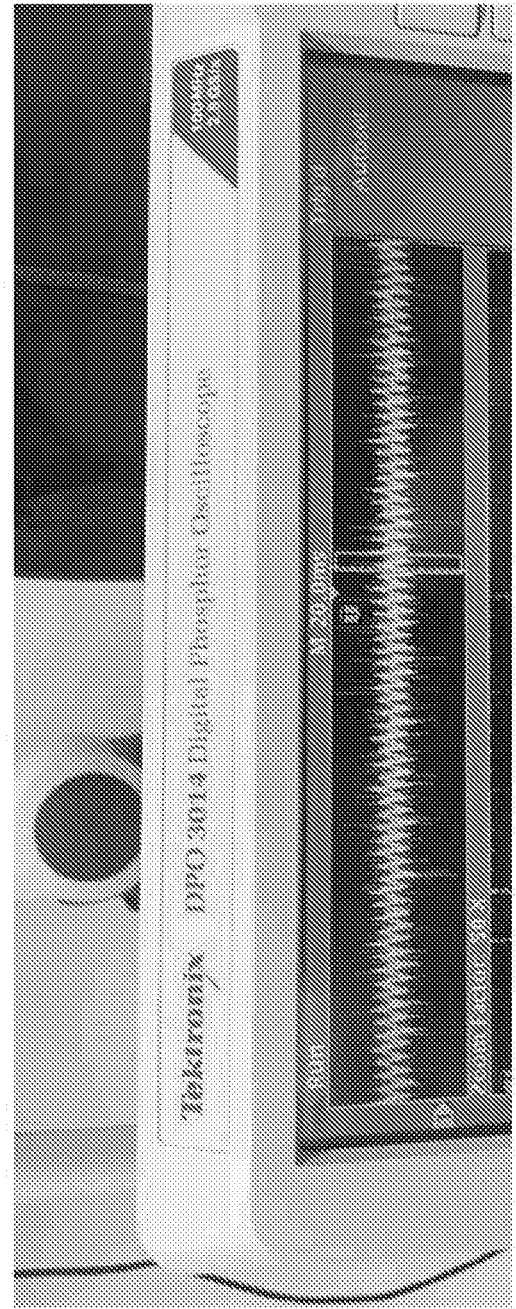
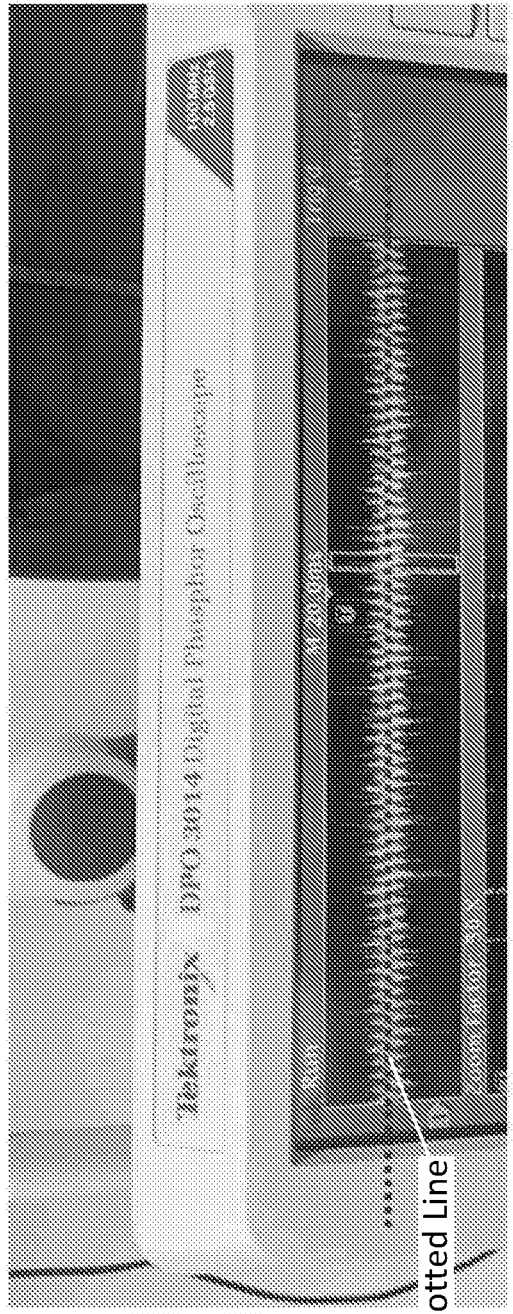
FIG. -6-

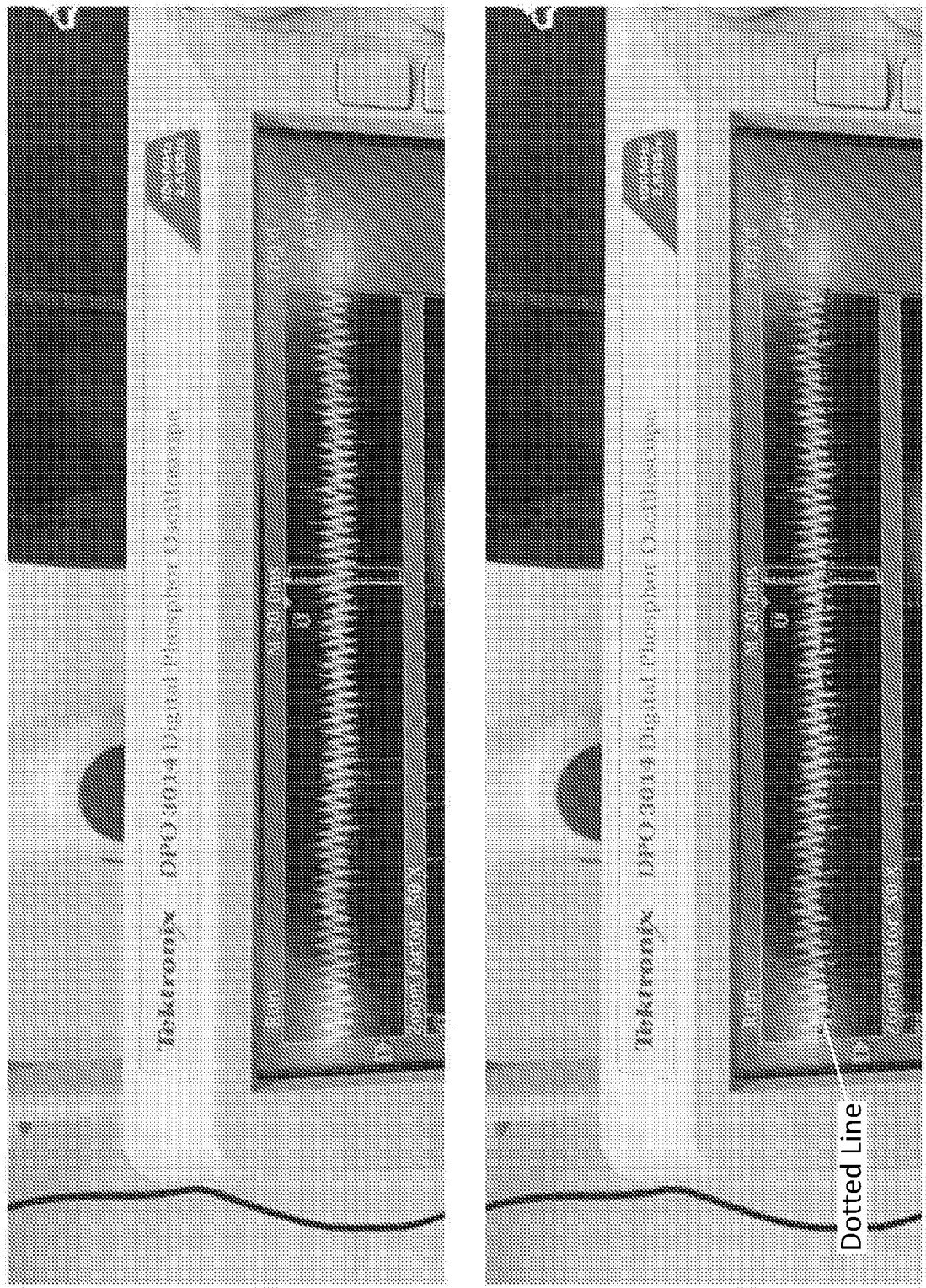
FIG. -7-

METHOD FOR DETECTING PRESENCE OF TUBING IN PUMP ASSEMBLY

FIELD

The present subject matter relates generally to pump assemblies and, more particularly, to methods and systems for detecting the presence of tubing in a pump head of a pump assembly.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the electrode-tissue interface, allowing a higher power to be applied without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion. Some systems including electrodes as described above may include multiple electrodes, each configured as a medical probe assembly. Thus, a cooling means may be provided for each of the plurality of probe assemblies, and typical cooling means include a pump assembly that pumps a cooling fluid to a probe assembly, at least in part through tubing loaded in a pump head of the pump assembly. In systems having multiple probe assemblies, each with an associated pump assembly, a typical approach is to operate all pump assemblies simultaneously, regardless of whether the associated probe assembly is being used in a procedure and, thus, requires cooling. Accordingly, known systems usually operate all pump heads even though one or more pump heads of the multiple pump assembly system may not be loaded with tubing.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of radiofrequency energy has also been used to treat tumors throughout the body. Further, with respect to knee pain, which also affects millions of individuals every year, high-frequency electrical treatment has been applied to several tissues, including, for example, the ligaments, muscles, tendons, and menisci.

Thus, the art is continuously seeking new and improved systems and methods for treating chronic pain using cooled RF ablation techniques. For example, improved systems utilizing one or more methods for detecting whether tubing is loaded in a pump assembly of the system, such that empty or unloaded pump assemblies can be deactivated or turned off, would be useful. As another example, systems having a controller for controlling a power supply to a pump assembly based on whether the pump assembly has tubing loaded in its pump head would be beneficial.

SUMMARY

Objects and advantages of the invention will be set forth in part in the following description, or may be obvious from the description, or may be learned through practice of the invention.

In one aspect, the present subject matter is directed to a method for detecting tubing in a pump assembly of a pump system. The method comprises connecting a power supply to each of a plurality of pump motors of the pump system. Each pump motor of the plurality of pump motors has a power supply cable configured to connect to the power supply. Further, each pump motor of the plurality of pump motors drives a pump head of a plurality of pump heads of the pump system. The method also comprises sensing a motor current from each of the power supply cables, determining whether tubing is loaded in each pump head, and, if tubing is not loaded in a pump head, then disconnecting from the power supply the power supply cable of the pump motor associated with the pump head in which tubing is not loaded. It should also be understood that the method may further include any of the additional features as described herein.

In another aspect, the present disclosure is directed to a system for detecting the presence of tubing within a pump head of a plurality of pump heads. The system comprises a plurality of pump assemblies. Each pump assembly comprises a pump motor, a power supply cable for supplying power to the pump motor, and one pump head of the plurality of pump heads. The pump motor drives the pump head. The system further comprises a controller for controlling whether power is supplied to the power supply cable of each pump assembly. The controller is configured for connecting a power supply to each power supply cable, sensing a motor current from each of the power supply cables, determining whether tubing is loaded in each pump head, and, if tubing is not loaded in a pump head, then disconnecting from the power supply the power supply cable of the pump motor associated with the pump head in which tubing is not loaded. It should also be appreciated that the system may further include any of the additional features as described herein.

In yet another aspect, the present disclosure is directed to a method for detecting tubing in a pump assembly. The method comprises connecting a power supply to a pump motor of the pump assembly. The pump motor has a power supply cable for connecting to the power supply, and the pump motor drives a pump head of the pump assembly. The method further comprises sensing a motor current from the power supply cable; transforming the motor current in a time domain to a frequency domain; determining whether tubing is loaded in the pump head and, if tubing is not loaded in the pump head, then disconnecting the power supply cable from the power supply; and calculating a speed of the pump motor if tubing is loaded in the pump head. Determining whether tubing is loaded in the pump head comprises determining how many fundamental frequencies are observable in the transformed motor current. It should also be understood that the method may further include any of the additional features as described herein.

These and other features, aspects and advantages of the present subject matter will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIG. 1 provides a schematic illustration of a portion of a system for applying radiofrequency electrical energy to a patient's body according to an exemplary embodiment of the present subject matter.

FIG. 2 provides a perspective view of a pump system of FIG. 1 according to an exemplary embodiment of the present subject matter.

FIG. 3 provides a block diagram of the pump system of FIG. 1 according to an exemplary embodiment of the present subject matter.

FIG. 4 provides a schematic diagram illustrating a portion of the pump system of FIG. 2 according to an exemplary embodiment of the present subject matter.

FIG. 5 provides a flow diagram illustrating a method for detecting tubing in a pump assembly according to an exemplary embodiment of the present subject matter.

FIG. 6 provides photographs of an oscilloscope screen, showing a current draw waveform for a pump assembly pump motor operating without tubing loaded in a pump head of the pump assembly.

FIG. 7 provides photographs of the oscilloscope screen of FIG. 6, showing a current draw waveform for the pump assembly pump motor operating with tubing loaded in the pump head of the pump assembly.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of the present subject matter, a lesion refers to the region of tissue that has been irreversibly damaged as a result of the application of thermal energy, and the present subject matter is not intended to be limited in this regard. Further, for the purposes of this description, proximal generally indicates that portion of a device or system next to or nearer to a user (when the device is in use), while the term distal generally indicates a portion further away from the user (when the device is in use).

Generally, the present subject matter provides pump systems, pump assemblies, and pump heads for pumping fluid to one or more systems or assemblies. More particularly, the present subject matter provides a pump system comprising a plurality of pump assemblies, and each pump assembly of the plurality of pump assemblies supplies a fluid to a cooling circuit. The cooling circuit may be used to supply cooling fluid to the distal end of a medical probe assembly for delivering energy to a patient's body, e.g., as part of a treatment procedure. The pump system further comprises a base for supporting the plurality of pump assemblies. Each pump assembly described herein comprises a pump head, a bezel surrounding an outer perimeter of the pump head, a motor, and tubing.

In general, the pump head comprises an occlusion bed, a rotor guide, a rotor assembly positioned between the occlusion bed and the rotor guide, and a pathway for tubing. The tubing supplies fluid to the cooling circuit. The pathway comprises an inlet portion, an outlet portion, and a connecting portion that connects the inlet portion to the outlet portion. The inlet portion of the pathway is defined between the occlusion bed and the rotor guide, the outlet portion of the pathway is defined between the occlusion bed and the rotor guide, and the connecting portion of the pathway is defined between the occlusion bed and the rotor assembly. Further, the occlusion bed is movable with respect to the rotor guide and the rotor assembly. As described herein, through such movement of the occlusion bed and other features, the pump head is configured to ease the task of inserting the tubing into the pump head such that correct insertion of the tubing is repeatable and safe. Once the tubing is inserted or loaded into the pump head, and the user is safely separated from the rotor assembly, e.g., by a rotor cover plate and pump head cover as described herein, the motor may be powered on to drive the rotor assembly and thereby begin pumping the fluid through the tubing.

Referring now to the drawings, FIG. 1 illustrates a schematic diagram of one embodiment of a system 100 of the present subject matter. As shown, the system 100 includes a generator 102; a cable 104; one or more probe assemblies 106 (only one probe assembly 106 is shown); one or more cooling devices 108; a pump cable 110; one or more proximal cooling supply tubes 112; and one or more proximal cooling return tubes 114. In an exemplary embodiment, the system 100 includes first, second, third, and fourth probe assemblies 106. As shown in the illustrated embodiment, the generator 102 is a radiofrequency (RF) generator, but optionally may be any power source that may deliver other forms of energy, including but not limited to microwave energy, thermal energy, ultrasound, and optical energy. Further, the generator 102 may include a display 103 (FIG. 2) incorporated therein. The display 103 may be operable to display various aspects of a treatment procedure, including but not limited to any parameters that are relevant to a treatment procedure, such as temperature, impedance, etc. and errors or warnings related to a treatment procedure. If no display 103 is incorporated into the generator 102, the generator 102 may include means of transmitting a signal to an external display. In one embodiment, the generator 102 is operable to communicate with one more devices, for example, with one or more of the probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two or more distal ends 132 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two or more distal ends 132 of the cable 104 terminate in connectors 134 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102. Alternatively, the splitter 130 may include more than two distal ends. Such a connector is useful in embodiments having more than two devices connected to the generator 102, for example, if more than two probe assemblies are being used.

The cooling device(s) 108 may include any means of reducing a temperature of material located at and proximate to one or more of the probe assemblies 106. For example, as shown in FIG. 2, the cooling devices 108 may include a pump system 120 having one or more peristaltic pump assemblies 122 operable to circulate a fluid from the cooling devices 108 through one or more proximal cooling supply tubes 112, the probe assemblies 106 (via internal lumens therein, as described in greater detail below), one or more proximal cooling return tubes 114 and back to the one or more cooling devices 108. For example, as shown in the illustrated embodiment of FIGS. 2 and 3, the pump system 120 includes four peristaltic pump assemblies 122 coupled to a power supply 126. In such embodiments, as shown in FIG. 3, each of the plurality of pump assemblies 122 may be in separate fluid communication with one of the probe assemblies. The fluid may be water or any other suitable fluid or gas. In alternate embodiments, the pump system 120 may include only one peristaltic pump assembly 122 or greater than four pump assemblies 122. In addition, as shown in FIG. 3, each of the pump assemblies 122 may have an independent speed (i.e., RPM) controller 125 that is configured to independently adjust the speed of its respective pump assembly. The pump system 120 and pump assemblies 122 are described in greater detail below.

Referring to FIG. 1, the system 100 may include a controller or control module 101 for facilitating communication between the cooling devices 108 and the generator 102. In this way, feedback control is established between the cooling devices 108 and the generator 102. The feedback control may include the generator 102, the probe assemblies 106, and the cooling devices 108, although any feedback between any two devices is within the scope of the present subject matter. The feedback control may be implemented, for example, in a control module that may be a component of the generator 102. In such embodiments, the generator 102 is operable to communicate bi-directionally with the probe assemblies 106 as well as with the cooling devices 108. In the context of the present subject matter, bi-directional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements. For example, power to each of the probe assemblies 106 can be increased when a temperature measurement is low or can be decreased when a measurement is high. This variation of power may be different for each probe assembly. In some cases, the generator 102 may terminate power to one or more probe assemblies 106. Thus, the generator 102 may receive a signal (e.g., temperature measurement) from one or both of the first and second probe assemblies 106, determine the appropriate action, and send a signal (e.g., decreased or increased power) back to one or both of the probe assemblies 106. Alternatively, the generator 102 may send a signal to the cooling devices 108 to either increase or decrease the flow rate or degree of cooling being supplied to one or both of the first and second probe assemblies 106.

More specifically, the pump assemblies 122 may communicate a fluid flow rate to the generator 102 and may receive communications from the generator 102 instructing the pumps 122 to modulate this flow rate. In some instances, the peristaltic pump assemblies 122 may respond to the generator 102 by changing the flow rate or turning off for a period of time. With the cooling devices 108 turned off, any temperature sensing elements associated with the probe assemblies 106 would not be affected by the cooling fluid, allowing a more precise determination of the surrounding tissue temperature to be made. In addition, when using more than one probe assembly 106, the average temperature or a maximum temperature in the temperature sensing elements associated with the probe assemblies 106 may be used to modulate cooling.

In other embodiments, the cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density. Thus, as illustrated by these examples, the controller 101 may actively control energy delivered to the tissue by controlling an amount of energy delivered through the energy delivery device(s) 192 and by controlling a flow rate through the pump assembly(ies) 122, e.g., the flow rate through tubing of a pump head 200 of a pump assembly 122.

The cooling devices 108 may also communicate with the generator 102 to alert the generator 102 to one or more possible errors and/or anomalies associated with the cooling devices 108. Such errors and/or anomalies may include whether cooling flow is impeded or if a lid of one or more of the cooling devices 108 is opened. The generator 102 may then act on the error signal by at least one of alerting a user, aborting the procedure, and modifying an action.

The controller 101, as well as the other controllers or microcontrollers described herein, such as the microcontroller 212 and motor controller 214, can include various components for performing various operations and functions. For example, the controller 101 can include one or more processor(s) and one or more memory device(s). The operation of the system 100, including the generator 102 and cooling device(s) 108, may be controlled by a processing device such as the controller 101, which may include a microprocessor or other device that is in operative communication with components of the system 100. In one embodiment, the processor executes programming instructions stored in memory and may be a general or special purpose processor or microprocessor operable to execute programming instructions, control code, or micro-control code. The memory may be a separate component from the processor or may be included onboard within the processor. Alternatively, the controller 101 may be constructed without using a processor or microprocessor, e.g., using a combination of discrete analog and/or digital logic circuitry (such as switches, amplifiers, integrators, comparators, flip-flops, AND gates, and the like) to perform control functionality instead of relying upon software. Components of the system 100 may be in communication with the controller 101 via one or more signal lines or shared communication busses.

Further, the one or more memory device(s) can store instructions that when executed by the one or more processor(s) cause the one or more processor(s) to perform the operations and functions, e.g., as those described herein for communicating a signal. In one embodiment, the generator 102 includes a control circuit having one or more processors and associated memory device(s) configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements.

Such memory device(s) may generally be configured to store suitable computer-readable instructions that, when implemented by the controller(s) or processor(s) 101, configure the control circuit to perform various functions including, but not limited to, controlling an amount of energy delivered through the energy delivery device(s) 192, controlling a flow rate through the pump assembly(ies) 122, and/or other functions. More particularly, the instructions may configure the control circuit to perform functions such as receiving directly or indirectly signals from one or more sensors (e.g. voltage sensors, current sensors, and/or other sensors) indicative of various input conditions, and/or various other suitable computer-implemented functions, which enable the generator 102 or other components of system 100 to carry out the various functions described herein. An interface can include one or more circuits, terminals, pins, contacts, conductors, or other components for sending and receiving control signals. Moreover, the control circuit may include a sensor interface (e.g., one or more analog-to-digital converters) to permit signals transmitted from any sensors within the system to be converted into signals that can be understood and processed by the controller(s) or processor(s) 101.

Still referring to FIG. 1, the proximal cooling supply tubes 112 may include proximal supply tube connectors 116 at the distal ends of the one or more proximal cooling supply tubes 112. Additionally, the proximal cooling return tubes 114 may include proximal return tube connectors 118 at the distal ends of the one or more proximal cooling return tubes 114. In one embodiment, the proximal supply tube connectors 116 are female luer-lock type connectors and the proximal return tube connectors 118 are male luer-lock type connectors, although other connector types are intended to be within the scope of the present subject matter.

In addition, as shown in FIG. 1, the probe assembly 106 may include a proximal region 160, a handle 180, a hollow elongate shaft 184, and a distal tip region 190 that includes the one or more energy delivery devices 192. The elongate shaft 184 and the distal tip region 190 together form a probe 186 that contact a patient's body to deliver energy thereto. The hollow elongate shaft 184 also may be described as an outer circumferential portion 184 of the probe 186, and the energy delivery device 192 extends distally from the outer circumferential portion 184. As further described herein, the elongate shaft 184 may be an electrically non-conductive outer circumferential portion 184, e.g., the shaft 184 may be formed from an electrically non-conductive material or may be electrically insulated, and the energy delivery device(s) 192 may be electrically and thermally-conductive energy delivery device(s) 192.

The proximal region 160 includes a distal cooling supply tube 162, a distal supply tube connector 166, a distal cooling return tube 164, a distal return tube connector 168, a probe assembly cable 170, and a probe cable connector 172. In such embodiments, the distal cooling supply tube 162 and distal cooling return tube 164 are flexible to allow for greater maneuverability of the probe assemblies 106 but alternate embodiments with rigid tubes are possible. Further, in several embodiments, the distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe assembly 106 also may include a shaft supply tube 136 and a shaft return tube 138, which are internal lumens for circulating cooling fluid to a distal end of the probe assembly 106. The distal cooling supply tube 162 and the distal cooling return tube 164 may be connected to the shaft supply tube 136 and the shaft return tube 138, respectively, within the handle 180 of the probe assembly 106. In one embodiment, the shaft supply tube 136 and the shaft return tube 138 may be hypotubes made of a conductive material, such as stainless steel, that extend from the handle 180 through a lumen of the hollow elongate shaft 184 to distal tip region 190. The number of hypotubes used for supplying cooling fluid and the number used for returning cooling fluid and the combination thereof may vary and all such combinations are intended to be within the scope of the present invention.

As illustrated in FIG. 1, the cooling fluid flows in a cooling circuit 140 formed by the cooling device(s) 108, the distal tip region 190 of the probe, and the various supply and return tubes 112, 114, 162, 162, 136, 138. The arrows FF in FIG. 1 illustrate the direction of flow of the cooling fluid supplied by the cooling device(s) 108 through the cooling circuit 140. More specifically, the cooling fluid flows from the cooling device(s) 108, through proximal cooling supply tube 112 to distal cooling supply tube 162, through distal cooling supply tube 162 to shaft supply tube 136, through shaft supply tube 136 to the distal tip region 190, from the distal tip region 190 to shaft return tube 138, through shaft return tube 138 to distal return tube 164, through distal return tube 164 to proximal return tube 114, and through proximal return tube 114 to the cooling device(s) 108.

Referring still to FIG. 1, the probe cable connector 172 may be located at a proximal end of the probe assembly cable 170 and may be operable to reversibly couple to one of the connectors 134, thus establishing an electrical connection between the generator 102 and the probe assembly 106. The probe assembly cable 170 may include one or more conductors depending on the specific configuration of the probe assembly 106. For example, in one embodiment, the probe assembly cable 170 may include five conductors allowing probe assembly cable 170 to transmit RF current from the generator 102 to the one or more energy delivery devices 192, as well as to connect multiple temperature sensing elements to the generator 102.

In addition, the handle 180 may be operable to easily and securely couple to an optional introducer tube, e.g., in an embodiment where an introducer tube would facilitate insertion of the one or more probe assemblies 106 into a patient's body. For instance, as shown, the handle 180 may taper at its distal end to accomplish this function, i.e., to enable the handle 180 to securely couple to an optional introducer tube. Generally, introducer tubes may include a proximal end, a distal end, and a longitudinal bore extending therebetween. Thus, the introducer tubes (when used) are operable to easily and securely couple with the probe assembly 106. For example, the proximal end of the introducer tubes may be fitted with a connector able to mate reversibly with the handle 180 of a probe assembly 106. An introducer tube may be used to gain access to a treatment site within a patient's body, and the hollow elongate shaft 184 of a probe assembly 106 may be introduced to the treatment site through the longitudinal bore of the introducer tube. Introducer tubes may further include one or more depth markers to enable a user to determine the depth of the distal end of the introducer tube within a patient's body. Additionally, introducer tubes may include one or more radiopaque markers to ensure the correct placement of the introducers when using fluoroscopic guidance.

The introducer tubes may be made of various materials, as is known in the art and, if the material is electrically conductive, the introducer tubes may be electrically insulated along all or part of their length, to prevent energy from being conducted to undesirable locations within a patient's body. In some embodiments, the elongate shaft 184 may be electrically conductive, and an introducer may function to insulate the shaft 184, leaving the energy delivery device 192 exposed for treatment. Further, the introducer tubes may be operable to connect to a power source and, therefore, may form part of an electrical current impedance monitor (wherein at least a portion of the introducer tube is not electrically insulated). Different tissues may have different electrical impedance characteristics, and therefore, it is possible to determine tissue type based on impedance measurements, as has been described. Thus, it would be beneficial to have a means of measuring impedance to determine the type of tissue within which a device is located. In addition, the gauge of the introducer tubes may vary depending on the procedure being performed and/or the tissue being treated. In some embodiments, the introducer tubes should be sufficiently sized in the radial dimension so as to accept at least one probe assembly 106. Moreover, in alternative embodiments, the elongate shaft 184 may be insulated so as not to conduct energy to portions of a patient's body that are not being treated.

The system 100 also may include one or more stylets. A stylet may have a beveled tip to facilitate insertion of the one or more introducer tubes into a patient's body. Various forms of stylets are well known in the art and the present subject matter is not limited to include only one specific form. Further, as described above with respect to the introducer tubes, the stylets may be operable to connect to a power source and may therefore form part of an electrical current impedance monitor. In other embodiments, one or more of the probe assemblies 106 may form part of an electrical current impedance monitor. Thus, the generator 102 may receive impedance measurements from one or more of the stylets, the introducer tubes, and/or the probe assemblies 106 and may perform an action, such as alerting a user to an incorrect placement of an energy delivery device 192, based on the impedance measurements.

The energy delivery devices 192 may include any means of delivering energy to a region of tissue adjacent to the distal tip region 190. For example, the energy delivery devices 192 may include an ultrasonic device, an electrode, or any other energy delivery means, and the present subject matter is not limited in this regard. Similarly, energy delivered via the energy delivery devices 192 may take several forms, including but not limited to thermal energy, ultrasonic energy, radiofrequency energy, microwave energy, or any other form of energy. For example, in one embodiment, the energy delivery devices 192 may include an electrode. The active region of the electrode 192 may be 2 to 20 millimeters (mm) in length and energy delivered by the electrode is electrical energy in the form of current in the RF range. The size of the active region of the electrode can be optimized for placement within, e.g., an intervertebral disc; however, different sizes of active regions, all of which are within the scope of the present subject matter, may be used depending on the specific procedure being performed. In some embodiments, feedback from the generator 102 may automatically adjust the exposed area of the energy delivery device 192 in response to a given measurement, such as impedance or temperature. For example, in one embodiment, the energy delivery devices 192 may maximize energy delivered to the tissue by implementing at least one additional feedback control, such as a rising impedance value. As previously described, each energy delivery device 192 may be electrically and thermally-conductive and may comprise a conductive outer circumferential surface to conduct electrical energy and heat from the distal tip region 190 of the probe 186 to a patient's body. Further, the distal tip region 190 includes one or more temperature sensing elements, which are operable to measure the temperature at and proximate to the one or more energy delivery devices 192. The temperature sensing elements may include one or more thermocouples, thermometers, thermistors, optical fluorescent sensors or any other means of sensing temperature.

In one embodiment, the first and second probe assemblies 106 may be operated in a bipolar mode. For example, the distal tip region 190 of each of two probe assemblies may be located within an intervertebral disc. In such embodiments, electrical energy is delivered to the first and second probe assemblies 106, and this energy is preferentially concentrated therebetween through a region of tissue to be treated (i.e., an area of the intervertebral disc). The region of tissue to be treated is thus heated by the energy concentrated between the first and second probe assemblies 106. In other embodiments, the first and second probe assemblies 106 may be operated in a monopolar mode, in which case an additional grounding pad is required on the surface of a body of a patient, as is known in the art. Any combination of bipolar and monopolar procedures may also be used. It should also be understood that the system may include more than two probe assemblies 100. For example, in some embodiments, three probe assemblies 106 may be used, and the probe assemblies 106 may be operated in a triphasic mode, whereby the phase of the current being supplied differs for each probe assembly 106. In further embodiments, the system 100 may be configured to control one or more of the flow of current between electrically conductive components and the current density around a particular component. In such embodiments, the system 100 may be configured to alternate between monopolar configurations, bipolar configurations, or quasi-bipolar configurations during a treatment procedure.

As a particular example, to treat tissue of a patient's body according to an exemplary embodiment of the present subject matter, the energy delivery device 192 of each of two probe assemblies 106 may be inserted into the patient's body, e.g., using an introducer and stylet as described herein. Once a power source, such as the generator 102, is connected to the probe assemblies 106, a stimulating electrical signal may be emitted from either of the electrodes 192 to a dispersive electrode or to the other electrode 192. This signal may be used to stimulate sensory nerves, where replication of symptomatic pain would verify that the tissue, such as an intervertebral disc, is pain-causing. Simultaneously, the cooling fluid may be circulated through the internal lumens 136, 138 of the probe assemblies 106 via the pump assemblies 122 and energy may be delivered from the RF generator 102 to the tissue through the energy delivery devices 192. In other words, radiofrequency energy is delivered to the electrodes 192 and the power is altered according to the temperature measured by the temperature sensing element in the tip of the electrodes 192 such that a desired temperature is reached between the distal tip regions 190 of the two probe assemblies 106. During the procedure, a treatment protocol such as the cooling supplied to the probe assemblies 106 and/or the power transmitted to the probe assemblies 106 may be adjusted and/or controlled to maintain a desirable treatment area shape, size and uniformity. More specifically, actively controlling energy delivered to the tissue by controlling both an amount of energy delivered through the energy delivery devices 192 and individually controlling the flow rate of the pump assemblies 122. In further embodiments, the generator 102 may control the energy delivered to the tissue based on the temperature measured by the temperature sensing element(s) in the distal tip region 190 of the probe assemblies 106 and/or based on impedance sensors.

Referring now to FIG. 4, a schematic diagram is provided of the pump system 120, according to an exemplary embodiment of the present subject matter. As shown in FIG. 4, the pump system 120 includes four pump assemblies 122. Each pump assembly 122 comprises a pump motor 150, a power supply cable 152 for supplying power to the pump motor 150, and a pump head 154 driven by the motor 150. Thus, the pump system 120 illustrated in FIG. 4 includes a first pump assembly 122*a* having a first motor 150*a*, a first power supply cable 152*a*, and a first pump head 154*a*; a second pump assembly 122*b* having a second motor 150*b*, a second power supply cable 152*b*, and a second pump head 154*b*; a third pump assembly 122*c* having a third motor 150*c*, a third power supply cable 152*c*, and a third pump head 154*c*; and a fourth pump assembly 122*d* having a fourth motor 150*d*, a fourth power supply cable 152*d*, and a fourth pump head 154*d*.

In each pump assembly 122, the motor 150 is directly coupled to the pump head 154 to drive the fluid pumping mechanism of the assembly 122, and the pump head 154 has a rotor assembly that may rotate clockwise or counterclockwise. A tubing 156 (FIG. 2) may be loaded into the pump head 154, and the pump head rotor assembly acts on, e.g., compresses, the tubing 156 to pump fluid from a fluid reservoir 158 (FIG. 2) through the tubing 156 and the cooling circuit 140, e.g., to cool the distal end 194 of the probe assembly 106. More particularly, in exemplary embodiments, the pump assemblies 122 are peristaltic pump assemblies. As such, for each pump assembly 122, tubing 156 extends through the pump head 154, and the pump head 154, driven by the motor 150, compresses the tubing 156 to draw a cooling fluid from the fluid reservoir 158 and pump the cooling fluid into the shaft supply tube or lumen 136 that delivers the cooling fluid to the distal end 194 of the energy delivery device 192 of the associated medical probe assembly 106, as previously described.

As described herein, the system 100 may comprise a plurality of probe assemblies 106 that each has a dedicated cooling circuit 140, where the flow of cooling fluid through the cooling circuit 140 is controlled by a pump assembly 122. That is, the number of pump assemblies 122 may match the number of medical probe assemblies 106; for example, the system 100 may include four probe assemblies 106 and four pump assemblies 122 as shown in FIGS. 2 and 4. However, not every probe assembly 106 of the system 100 may be operated during a procedure. For instance, a clinician may utilize only two probe assemblies 106 during a given procedure, such that only two probe assemblies 106 out of the four probe assemblies 106 require cooling via their cooling circuits 140. Therefore, for the pump assemblies 122 associated with probe assemblies 106 that are not in use during the procedure, it would be desirable to not run the pump motor 150 to drive the pump head 154, as no tubing 156 is loaded in the unused pump head 154 because no cooling is needed for the associated probe assembly 106.

As illustrated in FIG. 4, a control unit 148, such as a controller, processor, or the like that may have a memory and be configured for executing programming instructions as described above, is provided that helps determine whether tubing 156 is loaded into a pump head 154 and, if not, terminates power to the pump head 154. In some embodiments, the control unit 148 may be onboard the generator 102, e.g., the control unit 148 may be a control module of the controller 101. In other embodiments, the control unit 148 may be a separate controller or processor onboard the pump system 120 or other suitable component of the system 100. Further, the control unit 148 may be configured for controlling whether power is supplied to the power supply cable 152 of each pump assembly 122, e.g., by controlling whether a switch in each power supply line is open or closed, as described herein.

Referring to FIGS. 4 and 5, a method for detecting tubing in a pump assembly will be described, according to an exemplary embodiment of the present subject matter. FIG. 5 provides a flow diagram illustrating an exemplary method 500 for detecting tubing 156 in a pump assembly 122. As shown at 502 in FIG. 5, the method 500 includes connecting a power supply, such as power supply 126, to each of the plurality of pump motors 150 of the pump system 120. More specifically, the power supply cable 152 of each pump motor 150 is configured to connect to the power supply 126, such that, as shown in the exemplary embodiment of FIG. 4, each power supply cable 152a, 152b, 152c, 152d is connected to the power supply 126. At 502, the power supply cables 152 are placed in operative connection with the power supply 126 such that electrical current flows through each power supply cable 152. For instance, one or more switches or the like may be disposed between each power supply cable 152 and the power supply 126 such that the power or current may be interrupted to each power supply cable 152 individually. As an example, the power supply to the first power supply cable 152a, which provides power to the first pump motor 150a, may be interrupted or terminated, i.e., disconnected, thereby rendering the first pump motor 150a inoperable, while the power supply to each of the remaining power supply cables 152b, 152c, 152d is uninterrupted, i.e., the remaining power supply cables 152 are connected to the power supply 126. In some embodiments, the pump motors 150 may begin to operate as soon as the motors 150 are connected to the power supply 126, but in other embodiments, the method 500 also includes at 502 turning on the pump motors 150 when the motors 150 are connected to the power supply via the power supply cables 152.

As illustrated at 504 in FIG. 5, the method 500 further includes sensing a motor current from each of the power supply cables 152. Referring to FIG. 4, a current sensor 182 is connected to, or in operative communication with, each of the power supply cables 152 such that the current sensor 182 can measure the current draw by each pump motor 150. In some embodiments, the current sensor 182 simultaneously measures each supply current, but in other embodiments, the current sensor 182 multiplexes between each power supply cable 152 to measure the current and, thus, includes a multiplexer (or mux). In still other embodiments, the pump system 120 comprises a plurality of current sensors 182, and one current sensor 182 of the plurality of current sensors 182 is positioned at each power supply cable 152 of the plurality of power supply cables 152 to measure the current through the power supply cables 152. That is, an individual current sensor 182 may be provided to sense or measure the current draw by one pump motor 150, and an individual current sensor 182 is provided for each pump motor 150 of the pump system 120. Although primarily described herein with respect to a single current sensor 182, the present subject matter may be adapted for a plurality of current sensors 182, as will be readily understood by one having ordinary skill in the art.

The current sensor 182 is connected to the control unit 148 to communicate a motor current or motor current signal from each power supply cable 152 to the control unit 148. As depicted in FIG. 4, the control unit 148 of the exemplary embodiment includes three modules, engines, or software subroutines for processing the motor current signals—a filter 174, a fast Fourier Transform (FFT) engine 176, and a post-processing engine 178. Referring to FIG. 5, the method 500 includes at 506 passing the motor current from each of the power supply cables 152 through the filter 174 to produce a filtered current signal from each of the power supply cables 152. In various embodiments, the filter 174 may be a low-pass filter or a Kalman filter. A suitable filter 174 may be selected based on, e.g., a typical frequency of the motors 150, such that the filter 174 can filter out signal noise based on the motor 150. For instance, the motors 150 may be stepper motors, which exhibit a stepping frequency, and the cutoff frequency for the filter 174 may be based on the motor operating speed and step size.

As shown at 508 in FIG. 5, the method 500 also includes passing the filtered current signal from each of the power supply cables 152 through the FFT engine 176 to produce a transformed signal from each of the power supply cables 152. More specifically, the FFT engine 176 transforms the current measured from the power supply cables 152 in the time domain to the frequency domain. Next, as shown at 510, the method includes determining whether a tubing 156 is loaded in each pump head 154. In the depicted embodiment, the transformed signals pass from the FFT engine 176 to the post-processing engine 178, which determines whether the transformed signal from each power supply cable 152 contains one or two fundamental frequencies. More particularly, as illustrated in FIG. 6, when no tubing 156 is loaded in a pump head 154, the transformed current signal from the power supply cable 152 supplying the pump motor 150 associated with that pump head 154 exhibits only one fundamental frequency, which represents the stepping frequency of the motor 150. The waveform shown in the oscilloscope photographs of FIG. 6 is largely AC (alternating current) at a single fundamental frequency that represents the stepping frequency of the motor 150; the y-axis is the normalized current value and the x-axis is time. The upper and lower photographs in FIG. 6 are the same, but in the lower photograph, a dotted line has been added to more clearly delineate the waveform.

However, when tubing 156 is loaded in a pump head 154, the transformed current signal from the power supply cable 152 supplying the pump motor 150 associated with that pump head 154 exhibits two fundamental frequencies. The two fundamental frequencies represent the stepping frequency of the motor 150 and the frequency with which the pump head rotor assembly moves over the tubing 156, which is a lower frequency than the motor's stepping frequency. As shown in the oscilloscope photographs of FIG. 7, the stepping frequency of FIG. 6 is still present but is overlaid on a lower frequency. The lower frequency, representing the rotor assembly rollers moving over the tubing 156 as described, is called out by the dotted line in the lower photograph (which is otherwise identical to the upper photograph).

Thus, the post-processing engine 178 can use the presence of the lower frequency to determine that tubing is present in a pump head 154. Stated differently, if the post-processing engine 178 observes only one fundamental frequency in the transformed signal from a power supply cable 152 to a pump motor 150, then the post-processing engine 178 determines the pump head 154 associated with that pump motor 150 does not have tubing 156 loaded in the pump head 154. Then, as shown at 512, the associated pump motor 150 is disconnected from the power supply 126. That is, each pump head 154 without tubing 156 loaded in the pump head 154 does not need to be running and, therefore, the pump motor 150 driving such empty pump heads 154 can be stopped, turned off, or disconnected from the power supply 126. As previously discussed, the power supply 126 may be interrupted or terminated to a given pump motor 150 by, e.g., opening a switch in the power supply cable 152 supplying power to the motor 150.

Nonetheless, if the post-processing engine 178 observes two fundamental frequencies in the transformed signal from a power supply cable 152 to a pump motor 150, e.g., a higher frequency consistent with a stepper motor's stepping frequency and a lower frequency consistent with a rotor assembly rolling over a tube, then the post-processing engine 178 determines the pump head 154 associated with that pump motor 150 does have tubing 156 loaded in the pump head 154. Thus, the control unit 148 determines such pump motors 150 should remain connected to the power supply 126, and in some embodiments, the current sensor 182 may continue to sense the current through the connected power supply cables 152 and send the current signal(s) to the control unit 148 for processing. In some embodiments, as shown at 514, the lower frequency portion of the transformed current signal from a power supply cable 152 of a pump motor 150 driving a tubing-loaded pump head 154 also may be used to calculate or determine the speed, in revolutions per minute (RPM), of the pump motor 150. More specifically, the lower frequency, representing the frequency with which a roller of the pump head rotor assembly passes over the tubing 156, is determined from the transformed current signal and may be denoted f_L. The speed of the associated pump motor 150 may be calculated using the following equation:

$$RPM = \left(\frac{f\_L}{R}\right) \times 60$$

where R is the number of rollers on the pump head rotor assembly. Thus, the lower frequency f_L both denotes the presence of tubing 156 in the associated pump head 154 and can be used to determine the operating speed (or RPM) of the associated pump motor 150.

It will be appreciated that the foregoing method may be applied to each pump assembly 122 of the pump system 120 such that the pump motor(s) 150 of only the pump assembly(ies) 122 in which tubing is loaded are running during a procedure. As an example, at the beginning of a procedure utilizing two cooled probe assemblies 106, all of the pump assemblies 122 of the pump system 120 are connected to the power supply 126 such that all of the pump motors 150 begin to run or operate. Thus, in the depicted exemplary embodiments, four pump motors 150a, 150b, 150c, 150d are connected to the power supply 126 such that the motors 150 begin to run and drive their associated pump head 154. The current sensor 182 senses the current draw by each of the four pump motors, either simultaneously or by multiplexing as described herein, and send the current signal associated with each pump motor 150 to the control unit 148. The modules or engines of the control unit 148 process the current signals as described herein. Then, the control unit 148 determines whether the first pump head 154a is loaded with first tubing 156a, the second pump head 154b is loaded with second tubing 156b, the third pump head 154c is loaded with third tubing 156c, and the fourth pump head 154d is loaded with fourth tubing 156d. Because two cooled probe assemblies 106 are being used in the procedure as stated above, only two of the pump heads 154 are loaded with tubing 156, so by analyzing the current signals from all four pump motors 150, the control unit 148 determines which two pump heads 154 are loaded and disconnects the pump motors 150 associated with the remaining two pump heads 154 from the power source 126. For example, if the control unit 148 determines the second and fourth pump heads 154b, 154d are loaded with tubing, the control unit 148 disconnects the first and third pump motors 150a, 150c from the power supply 126, e.g., by opening a switch in the first and third power supply cables 152a, 152c. Further, as described with respect to method 500, the control unit 148 may determine the operating speed of the second and fourth pump motors 150b, 150d using the lower fundamental frequency.

Detecting tubing using only pump motor supply current thresholds would be challenging due to the minute difference in supply current thresholds between a pump head 154 operating with tubing 156 and a pump head 154 operating without tubing 156. For instance, for a pump head 154 rotating at 140 RPM, a pump motor 150 may draw on average 300 mA (300 milliamps) without tubing 156 and approximately 310 mA (310 milliamps) with tubing 156, within a noise floor of 10-20 mA (10-20 milliamps). Thus, it is not possible to effectively and repeatedly distinguish between a loaded and unloaded pump head 154 using only the difference in pump motor supply current.

Accordingly, the present subject matter provides a system and method for detecting whether tubing is present in a pump head of a pump assembly, using an effective and repeatable approach. More particularly, the difference in the pump motor supply current waveform between loaded and unloaded pump heads is used to detect the presence of tubing. As described herein, in exemplary embodiments, the method comprises operating (or turning on) all pump motors of the pump system and observing the fundamental frequencies (or waveforms) detectable in the current draw by each pump motor. If tubing is not detected in a pump head, that pump motor is rendered inoperable (or turned off), e.g., by disconnecting the pump motor from its power supply. If tubing is detected in a pump head, the pump motor associated with that pump head remains operable (or turned on) such that cooling fluid may be pumped through the tubing. Thus, only those pump motors of the pump assemblies actually in use during a procedure utilizing the cooling fluid are operated or activated (or turned on) for the majority of the procedure.

Deactivating the pump motors of the unused pump assemblies reduces the power or energy consumption of the system and reduces wear on the pump assemblies by running the assemblies only when needed. Further, the safety of the system may be enhanced by reducing the number of rotating parts, e.g., it is far less likely that an object will get twisted or tangled up in a rotor or rotor assembly that is not rotating, and the pump motor rotor and pump head rotor assembly of deactivated pump assemblies are not rotating. Moreover, because the method for detecting the presence of tubing essentially comprises using the difference in the supply current waveform between loaded and unloaded pump heads to determine whether a given pump head is loaded or unloaded, the approach described herein may be implemented in some systems without the addition of any hardware. That is, the method is implemented through software, and the system need only a current sensor (which may be a standard hardware component of the system) to provide the necessary inputs to the software to implement the method. Thus, the method described herein may be a relatively low cost approach to ensuring only the needed pump assemblies are operated during a procedure. In addition, the method for detecting tubing described herein also provides means for assessing during operation the rotational speed of the pump motors or pump heads that are loaded with tubing. Other benefits and advantages of the present subject matter also may be realized by those of ordinary skill in the art.

Moreover, a system of the present subject matter may be used in various medical procedures where usage of an energy delivery device may prove beneficial. Specifically, the system of the present subject matter is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

Using liquid-cooled probe assemblies 106 with an appropriate feedback control system as described herein also contributes to the uniformity of the treatment. The cooling distal tip regions 190 of the probe assemblies 106 helps to prevent excessively high temperatures in these regions which may lead to tissue adhering to the probe assemblies 106 as well as an increase in the impedance of tissue surrounding the distal tip regions 190 of the probe assemblies 106. Thus, by cooling the distal tip regions 190 of the probe assemblies 106, higher power can be delivered to tissue with a minimal risk of tissue charring at or immediately surrounding the distal tip regions 190. Delivering higher power to energy delivery devices 192 allows tissue further away from the energy delivery devices 192 to reach a temperature high enough to create a lesion and thus the lesion will not be limited to a region of tissue immediately surrounding the energy delivery devices 192 but will rather extend preferentially from a distal tip region 190 of one probe assembly 106 to the other.

As has been mentioned, a system of the present subject matter may be used to produce a relatively uniform lesion substantially between two probe assemblies 106 when operated in a bipolar mode. Oftentimes, uniform lesions may be contraindicated, such as in a case where a tissue to be treated is located closer to one energy delivery device 192 than to the other. In cases where a uniform lesion may be undesirable, using two or more cooled probe assemblies 106 in combination with a suitable feedback and control system may allow for the creation of lesions of varying size and shape. For example, preset temperature and/or power profiles that the procedure should follow may be programmed into the generator 102 prior to commencement of a treatment procedure. These profiles may define parameters (these parameters would depend on certain tissue parameters, such as heat capacity, etc.) that should be used to create a lesion of a specific size and shape. These parameters may include, but are not limited to, maximum allowable temperature, ramp rate (i.e. how quickly the temperature is raised) and the rate of cooling flow, for each individual probe. Based on temperature or impedance measurements performed during the procedure, various parameters, such as power or cooling, may be modulated, to comply with the preset profiles, resulting in a lesion with the desired dimensions.

Similarly, it is to be understood that a uniform lesion can be created, using a system of the present subject matter, using many different pre-set temperature and/or power profiles which allow the thermal dose across the tissue to be as uniform as possible, and that the present subject matter is not limited in this regard.

It should be noted that the term radiopaque marker as used herein denotes any addition or reduction of material that increases or reduces the radiopacity of the device. Further, the terms probe assembly, introducer, stylet etc. are not intended to be limiting and denote any medical and surgical tools that can be used to perform similar functions to those described. In addition, the subject matter is not limited to be used in the clinical applications disclosed herein, and other medical and surgical procedures wherein a device of the present subject matter would be useful are included within the scope of the present subject matter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A method for detecting tubing in a pump assembly, the pump assembly comprising a motor that drives a pump head, the method comprising:

measuring a motor current from a power supply cable that electrically couples the motor of the pump assembly to a power supply as the pump assembly is operating;

generating a filtered motor current signal by passing the measured motor current through a digital filter;

generating a frequency domain representation of the filtered motor current signal;

determining whether the tubing is loaded into the pump head of the pump assembly based on the frequency domain representation of the filtered motor current signal; and terminating power delivery to the motor if it is determined that the tubing is not loaded into the pump head.

2. The method of claim 1, wherein the digital filter is a low-pass filter.

3. The method of claim 1, wherein the digital filter is a Kalman filter.

4. The method of claim 1, wherein generating the frequency domain representation of the filtered motor current signal comprises passing the filtered motor current signal through a fast Fourier Transform (FFT) engine.

5. The method of claim 1, wherein determining whether the tubing is loaded into the pump head of the pump assembly identifying fundamental frequencies in the frequency domain representation of the filtered motor current signal.

6. The method of claim 5, wherein it is determined that the tubing is not loaded into the pump head if only one fundamental frequency is identified.

7. The method of claim 5, wherein it is determined that the tubing is loaded into the pump head if two fundamental frequencies are identified.

8. The method of claim 1, further comprising calculating a speed of the motor if it is determined that the tubing is loaded into the pump head.

9. The method of claim 8, wherein the speed of the motor is calculated as $$\frac{f\_L}{R} \times 60,$$

where R is a number of roller in a rotor assembly of the pump head and f_L is a lower of at least two fundamental frequency identified in the frequency domain representation of the filtered motor current signal.

10. The method of claim 1, wherein the pump assembly is a peristaltic pump assembly.

11. The method of claim 1, wherein the pump assembly is configured to transfer cooling fluid to a medical probe assembly for cooled radiofrequency ablation.

12. A method for detecting tubing in a pump assembly, the pump assembly comprising a motor that drives a pump head, the method comprising:

measuring a motor current from a power supply cable that electrically couples the motor of the pump assembly to a power supply as the pump assembly is operating;

generating a filtered motor current signal by passing the measured motor current through a digital filter;

generating a frequency domain representation of the filtered motor current signal;

determining whether the tubing is loaded into the pump head of the pump assembly based on the frequency domain representation of the filtered motor current signal; and calculating a speed of the motor if it is determined that the tubing is loaded into the pump head.

13. The method of claim 12, wherein the digital filter is one of a low-pass filter or a Kalman filter.

14. The method of claim 12, wherein generating the frequency domain representation of the filtered motor current signal comprises passing the filtered motor current signal through a fast Fourier Transform (FFT) engine.

15. The method of claim 12, wherein determining whether the tubing is loaded into the pump head of the pump assembly identifying fundamental frequencies in the frequency domain representation of the filtered motor current signal.

16. The method of claim 15, wherein it is determined that the tubing is not loaded into the pump head if only one fundamental frequency is identified.

17. The method of claim 15, wherein it is determined that the tubing is loaded into the pump head if two fundamental frequencies are identified.

18. The method of claim 12, wherein the pump assembly is a peristaltic pump assembly.

19. The method of claim 12, wherein the pump assembly is configured to transfer cooling fluid to a medical probe assembly for cooled radiofrequency ablation.

20. A controller for a pump assembly, the pump assembly comprising a motor that drives a pump head, the controller configured to:

measure a motor current from a power supply cable that electrically couples the motor of the pump assembly to a power supply as the pump assembly is operating;

generate a filtered motor current signal by passing the measured motor current through a digital filter;

generate a frequency domain representation of the filtered motor current signal;

determine whether tubing is loaded into the pump head based on the frequency domain representation of the filtered motor current signal; and either:

terminate power delivery to the motor if it is determined that the tubing is not loaded into the pump head; or calculate a speed of the motor if it is determined that the tubing is loaded into the pump head.

* * * * *